(12) United States Patent
Kondo

(10) Patent No.: US 6,329,061 B2
(45) Date of Patent: *Dec. 11, 2001

(54) LAMINATED GLASS WITH FUNCTIONAL ULTRA-FINE PARTICLES AND METHOD OF PRODUCING SAME

(75) Inventor: Takeshi Kondo, Matsusaka (JP)

(73) Assignee: Central Glass Company, Limited, Ube (JP)

(*) Notice: Subject to any disclaimer, the term of this patent is extended or adjusted under 35 U.S.C. 154(b) by 0 days.

This patent is subject to a terminal disclaimer.

(21) Appl. No.: 09/842,676

(22) Filed: Apr. 27, 2001

Related U.S. Application Data

(62) Division of application No. 09/133,820, filed on Aug. 13, 1998, which is a division of application No. 08/588,963, filed on Jan. 19, 1996, now Pat. No. 5,830,568.

(30) Foreign Application Priority Data

Jan. 23, 1995 (JP) .......................................... 7-7944
Jun. 30, 1995 (JP) .......................................... 7-165489

(51) Int. Cl.$^7$ .............................. B32B 5/16; B32B 17/10; B32B 17/06
(52) U.S. Cl. .................. 428/432; 428/441; 428/442; 428/328; 428/436; 428/437; 428/699; 428/702; 428/407; 428/329; 428/331
(58) Field of Search ................... 428/432, 441, 428/442, 328, 436, 437, 699, 702, 329, 331, 407; 52/204.5; 296/84.1

(56) References Cited

U.S. PATENT DOCUMENTS

| 3,405,425 | 10/1968 | Buckley et al. . |
|---|---|---|
| 5,518,810 | 5/1996 | Nishihara et al. . |
| 5,742,118 | 4/1998 | Endo et al. . |
| 5,830,568 | * 11/1998 | Kondo . |

FOREIGN PATENT DOCUMENTS

| 0 227 631 A2 | 7/1987 | (EP) . |
|---|---|---|
| 0 578 829 A1 | 1/1994 | (EP) . |
| 2 579 976 | 10/1986 | (FR) . |
| 1124254 | 8/1968 | (GB) . |
| 52-78225 | 7/1977 | (JP) . |
| 61-141616 | 6/1986 | (JP) . |
| 63-281837 | 11/1988 | (JP) . |
| 2-22152 | 1/1990 | (JP) . |
| 2-136230 | 5/1990 | (JP) . |
| 4-160041 | 6/1992 | (JP) . |
| 4-261842 | 9/1992 | (JP) . |
| 5-70178 | 3/1993 | (JP) . |
| 6-329446 | 11/1994 | (JP) . |
| WO 92/16369 | 10/1992 | (WO) . |

OTHER PUBLICATIONS

Patent Abstracts of Japan, vol. 12, No. 132 (C–490), JP 62 252347 A, Tomita Takashi, Nov. 4, 1987.
Patent Abstracts of Japan, vol. 14, No. 171, (C–0706), JP 02 022152 A, Tsukamoto Michinori, Jan. 25, 1990.
Patent Abstracts of Japan, vol. 17, No. 43 (M–1360), JP 04 261842 A, Omura Hirobumi, Sep. 17, 1992.
Patent Abstracts of Japan, vol. 16, No. 455 (C–0987), JP 04 160041 A, Degawa Taku, Jun. 3, 1992.
Patent Abstracts of Japan, vol. 95, No. 004, JP 07 024957 A, Iida Shigeki, Jan. 27, 1995.
Derwent Publications Ltd., Section Ch, Week 8510, JP 60 016 840 A, Sekisui Chem. Ind. Co. Ltd., Jan. 28, 1985.
Derwent Publications Ltd., Section Ch, Week 8333, JP 58 117 228 A, Mitsubishi Monsanto KK et al., Jul. 12, 1983.

* cited by examiner

Primary Examiner—Deborah Jones
Assistant Examiner—Jennifer McNeil
(74) Attorney, Agent, or Firm—Crowell & Moring LLP

(57) ABSTRACT

The invention provides a laminated glass and a method of producing the same. This laminated glass includes first and second transparent glass plates and an interlayer film interposed therebetween. This interlayer film has functional ultra-fine particles which have a particle diameter of up to 0.2 $\mu$m and are dispersed therein. Due to the incorporation of the ultra-fine particles thereinto, the interlayer film is provided with various additional functions such as heat insulation, ultraviolet ray absorption and the maintenance of a sufficient radio transmittance. Therefore, the laminated glass becomes suitable as an architectural or automotive laminated glass.

14 Claims, No Drawings

LAMINATED GLASS WITH FUNCTIONAL ULTRA-FINE PARTICLES AND METHOD OF PRODUCING SAME

This application is a division of application Ser. No. 09/133,820, filed Aug. 13, 1998, which is a divisional of Ser. No. 08/588,963, filed on Jan. 19, 1996 (now U.S. Pat. No. 5,830,568).

BACKGROUND OF THE INVENTION

The present invention relates to a laminated glass with an interlayer resinoid film containing functional ultra-fine particles dispersed therein and a method of producing this laminated glass.

There have been proposed colorless or colored architectural glasses having functions of heat insulation, ultraviolet ray insulation and improved radio wave transmission. Furthermore, there have been proposed automotive glasses having a function of heat insulation for insulating solar radiation energy incident on car interior and thus for lowering the air conditioning load, and a function of ultraviolet ray insulation. Recently, there has been an increasing demand for an architectural or automotive laminated glass having functions of heat insulation, ultraviolet ray insulation, and improved radio wave transmission, while this glass has a sufficient visible light transmittance.

There are several proposals that fine particles are contained in the interlayer film of laminated glass, for providing the laminated glass with a certain function(s). For example, Japanese Patent Unexamined Publication JP-A-2-22152 discloses an interlayer film of laminated glass, for insulating short wavelength light rays. This interlayer film is made of a plasticized polyvinyl butyral containing at least one light absorbing agent selected from special benzotriazole derivatives and an inorganic matter in the form of fine powder. 90% by weight of this inorganic matter has a particle diameter within a range from 250 to 400 nm. This interlayer film is characterized in that light rays of up to 400 nm wavelength is substantially insulated and that light rays of at least 450 nm wavelength is substantially transmitted therethrough. The light absorbing agent's content is from 0.4 to 6 wt %, and the inorganic matter's content is from 2 to 17 wt %.

As another example, Japanese Patent Unexamined Publication JP-A-4-160041 discloses an automotive window glass having a layer interposed between transparent platelike members. This layer is made of a mixture of a glass component and ultra-fine particles having an average diameter of up to 0.1 $\mu$m. The glass component is an organic silicon or an organic silicon compound and serves to bond together at a relatively low temperature two glass plates of a laminated glass or an inter resinoid film and a glass plate. The ultra-fine particles has a function of transparent electric conductiveness, infrared reflection function, electromagnetic insulation function.

Japanese Patent Unexamined Publication JP-A-4-261842 discloses a laminated glass comprising an organic glass member, a transparent member, and an interlayer film interposed therebetween. This interlayer film contains 100 parts by weight of an ethylene-ethylacrylate copolymerized resin prepared by graft modification of a vinylsilane and 3–30 parts by weight of optional silicon dioxide fine particles. When the particle diameter of the fine particles is from 0.1 to 400 nm, scatter of light rays which are transmitted through the interlayer film can be prevented.

SUMMARY OF THE INVENTION

It is an object of the present invention to provide a laminated glass which has a good quality requisite for an architectural or automotive laminated glass itself and of which interlayer film has various additional functions such as heat insulation, ultraviolet ray absorption and the maintenance of a sufficient radio transmittance.

According to a first aspect of the present invention, there is provided a laminated glass comprising:

first and second transparent glass plates;

an interlayer film interposed between said first and second glass plates; and functional ultra-fine particles which have a particle diameter of up to 0.2 $\mu$m and are dispersed in said interlayer film.

According to a second aspect of the present invention, there is provided a method of. producing a laminated glass, comprising the steps of:

(a) interposing an interlayer film between first and second glass plates, said interlayer film having functional ultra-fine particles which are dispersed therein and have a particle diameter of up to 0.2 $\mu$m; and (b) bonding together said first and second glass plates and said interlayer film.

As is mentioned above, a laminated glass according to the present invention has an interlayer film containing ultra-fine particles which have a particle diameter of up to 0.2 $\mu$m and are dispersed in the interlayer film. With this, the laminated glass has various additional functions such as the provision of colorlessness or a certain desired color tone, heat insulation, ultraviolet ray insulation, the maintenance of a sufficient radio transmittance, and the like, without adding an adverse effect on the interlayer film's basic characteristics requisite for an architectural or automotive laminated glass. Therefore, the laminated glass is capable of improving the air conditioning effect and inhabitability of automobile, building and the like, of reducing an adverse effect of ultraviolet rays on the interior of automobile, building or the like, and of maintaining a sufficient radio transmittance equivalent to that of a conventional float glass, for receiving and transmitting radio waves.

A laminated glass according to the present invention is well controlled in color tone, extremely low in haze value, and superior in transparency and in reduction of reflection and glare. For example, the laminated glass has requisite basic characteristics for an automotive safety glass. These basic characteristics are substantially equivalent to those of conventional automotive laminated glass and provide satisfactory results in various tests- of Japanese Industrial Standard (JIS) R 3212 and the like.

In a method of producing a laminated glass according to the present invention, it is not necessary to use a glass plate having a special composition nor a glass plate having a special surface finish. A conventional production line for producing conventional laminated glasses can be used for producing a laminated glass of the present invention. Therefore, the laminated glass can be easily and economically produced. Furthermore, it can be flexibly produced according to the size and shape of the laminated glass.

DESCRIPTION OF THE PREFERRED EMBODIMENTS

In the following, a laminated glass according to the present invention will be described in detail. This laminated glass comprises first and second transparent glass plates and an interlayer film interposed therebetween. The interlayer film has functional ultra-fine particles which have a particle diameter of up to 0.2 $\mu$m and are dispersed therein. These particles are used to provide various functions such as heat insulation, thereby maintaining the solar radiation transmittance within a range of up to 65%, while the scattering and reflection of the visible light rays is suppressed. In spite of the fact that the interlayer film contains the functional ultra-fine particles, it has been unexpectedly found that the laminated glass has an extremely low haze value, a good radio transmittance and a sufficient transparency and that the interlayer film is sufficient in bond strength against the first and second glass plates, in transparency, durability and the like. Even though the interlayer film contains the functional ultra-fine particles, the laminated glass can be produced in a production line for conventional laminated glasses. The functional ultra-fine particles have a particle diameter preferably up to 0.15 $\mu$m or from 0.001 to 0.2 $\mu$m, more preferably from 0.001 to 0.15 $\mu$m or from 0.002 to 0.15 $\mu$m, and still more preferably from about 0.001 to about 0.10 $\mu$m or from about 0.002 to about 0.10 $\mu$m. It is preferable that these particles have a narrow particle diameter distribution, for example, within a range about 0.01 to about 0.03 $\mu$m.

In the invention, it is preferable that the functional ultra-fine particles amount to up to 10.0 wt % based on the total weight of the interlayer film. With this, these particles have various functions such as heat insulation, for example, to maintain the solar radiation transmittance within a range of up to 65%, while a first condition that the laminated glass has an extremely low haze value, a sufficient radio transmittance and a sufficient transparency is satisfied, while a second condition that the interlayer film is sufficient in bond strength against the first and second glass plates, in transparency, durability and the like is satisfied, and while a third condition that the laminated glass can be produced by a production line for conventional laminated glasses is satisfied. If the amount of the functional ultra-fine particles exceeds 10.0 wt %, it becomes difficult to satisfy the above-mentioned first, second and third conditions. When the laminated glass is used as an architectural glass having a visible light transmittance (Tv) of at least 35%, it is necessary to add the ultra-fine particles made of inorganic pigment(s) in an amount within a range from about 0.1 to about 10 wt %. In general, in the production of the laminated glass as an architectural glass, the amount of the ultra-fine particles is preferably from about 0.01 to about 9 wt % and more preferably from about 0.05 to about 8 wt %. In general, in the production of the laminated glass as an automotive glass, the amount of these particles is preferably from about 0.01 to about 2.0 wt % and more preferably from about 0.1 to about 1.0 wt %. In conclusion, the amount of these particles is decided according to the balance between the above-mentioned additional functions of these particles and the basic characteristics of the laminated glass. That is, if the amount of these particles is too much, the additional functions of these particles become sufficient, but the basic characteristics of the laminated glass may be impaired. On the contrary, if the amount of these particles is too little, the basic characteristics of the laminated glass are maintained, but the additional functions of these particles become insufficient.

In the invention, the interlayer film is not limited to a particular material, but preferably made of a polyvinyl butyral (PVB) or an ethylene-vinylacetate copolymer (EVA), which is generally used as a material for the interlayer film. Examples of the material of the interlayer film are a plasticized PVB made by Sekisui Chemical Industries, Ltd., Monsant Japan, Ltd. or the like, an EVA made by Du pont Co. or Takeda Chemical Industries, Ltd. (DUMILAN (trade name)), and a modified EVA (e.g., MERUCENE G (trade name) made by Toso Co.). It is optional to add an additive(s) to the interlayer film, such as ultraviolet absorbing agent, antioxidant, antistatic agent, heat stabilization agent, lubricant, filler, coloring agent, and bond adjusting agent.

It is optional that the interlayer film according to the present invention is placed on a conventional interlayer film to prepare a laminate, and then this laminate is interposed between the first and second glass plates to prepare the laminated glass. Furthermore, it is optional that the interlayer film according to the present invention is interposed between first and second conventional interlayer films to prepare a laminate to be interposed between the first and second glass plates.

In the invention, it is preferable that the functional ultra-fine particles comprise at least one member selected from the group consisting of metals, compounds containing the metals, and composites containing the metals. These metals consist of Sn, Ti, Si, Zn, Zr, Fe, Al, Cr, Co, Ce, In, Ni, Ag, Cu, Pt, Mn, Ta, W, V and Mo. The compounds containing the metals consist of oxides of the metals, nitrides of the metals, oxynitrides of the metals, and sulfides of the metals. The composites containing the metals consist of the metals doped with at least one substance, and the compounds doped with the at least one substance. The at least one substance is selected from the group consisting of antimony, antimony compounds, fluorine, fluorine compounds, stannous compounds, and aluminum compounds. The functional ultra-fine particles may comprise a mixture of the above-mentioned at least one member and an organic resin. This mixture may be the at least one member coated with this organic resin.

Examples of the above-mentioned oxides of the metals for the functional ultra-fine particles are $SnO_2$, $TiO_2$, $SiO_2$, $ZrO_2$, $ZnO$, $Fe_2O_3$, $Al_2O_3$, $FeO$, $Cr_2O_3$, $Co_2O_3$, $CeO_2$, $In_2O_3$, $NiO$, $MnO$ and $CuO$. Exemplary commercial products of the functional ultra-fine particles made of $TiO_2$ are IT-S-UD (trade name) which is made by Idemitsu Petrochemical Co., Ltd. and has a particle diameter of 0.02 $\mu$m, and UF01 (trade name) which is made by Tai Oxide Chemicals Co. and has a particle diameter of 0.018 $\mu$m. An exemplary commercial product of the functional ultra-fine particles made of $Fe_2O_3$ is NANOTITE (trade name) which is in the form of spherical ultra-fine hematite particles, has a particle diameter of 0.06 $\mu$m and is made by Showa Denko K.K. Examples of the above-mentioned nitrides of the metals are TiN and AlN. An example of the above-mentioned sulfides of the metals is ZnS. Examples of the metals with doped with the at least one substance are $SnO_2$ doped with 9 wt % $Sb_2O_3$ (ATO) made by Sumitomo Osaka Cement Co., $SnO_2$ doped with fluorine, and $SnO_2$ doped with 10 wt % $Sb_2O_3$. Examples of mixtures (composites) each containing at least two of the above-mentioned metals are $In_2O_3$–5 wt % $SnO_2$ (ITO) made by Mitsubishi Material Co., and inorganic pigment ultra-fine particles such as $Co_2O_3$—$Al_2O_3$ (e.g., TM3410 (trade name) having a particle diameter from 0.01 to 0.02 $\mu$m), $TiO_2$—NiO—$Co_2O_3$—ZnO (e.g., TM3320 (trade name) having a particle diameter from 0.01 to 0.02 $\mu$m) and $Fe_2O_3$—ZnO—$Cr_2O_3$ (e.g., TM3210 (trade name) having a particle diameter from 0.01 to 0.02 $\mu$m). TM3410, TM3320 and TM3210 are made by Dai Nichi Seika Kogyo Co. Examples of the above-mentioned organic resin to be used together with the above-mentioned at least one member are fluorine compounds such as fluororesins, polytetrafluoroethylene (PTFE), LUBURON (trade name) made by Daikin Industries, Ltd., CEFRAL LUBE (trade name) of Central Glass Co., Ltd., and low molecular weight trifluoroethylene (TFE), silicone resins, silicone rubbers. Of the above examples, ATO and ITO are particularly preferable examples as the functional ultra-fine particles for an automotive laminated glass.

The above-mentioned organic resin is used to reduce bond strength between the PVB film and the first and second glass plates. In other words, in case that, for example, ATO or ITO is used as the functional ultra-fine particles, the bond strength may become too much. In this case, the organic resin is used to lower the pummel value and thus to reduce the bond strength to a permissible standard range. Thus, the purpose of the addition of the organic resin is similar to that of the primer coating on the glass plate surface or to that of the coating of the organic resin film made of fluororesin, silicone resin, silicone rubber or the like.

By the incorporation of the functional ultra-fine particles into the interlayer film, the laminated glass is provided with various functions such as heat insulation, ultraviolet ray insulation, the provision of colorlessness or a certain desired color tone, light insulation and the like.

In the invention, the interlayer may contain an organic ultraviolet-ray-absorbing agent. Examples of this agent are benzotriazole derivatives such as 2-(2'-hydroxy-5'-methylphenyl)benzotriazole, 2-(2'-hydroxy-3',5'-ditertbutylphenyl)benzotriazole, 2-(2'-hydroxy-3'-tert-butyl-5'-methylphenyl)-5-chlorobenzotriazole, 2-(2'-hydroxy-3', 5'-ditertbutylphenyl)-5-chlorobenzotriazole and 2-(2'-hydroxy-3',5'-ditert-amylphenyl)benzotriazole, benzophenone derivatives such as 2,4-dihydroxybenzophenone, 2-hydroxy-4-methoxybenzophenone, 2-hydroxy-4-octoxybenzophenone, 2-hydroxy-4-dodecyloxybenzophenone, 2,2'-dihydroxy-4-methoxybenzophenone, 2,2'-dihydroxy-4,4'-dimethoxybenzophenone and 2-hydroxy-4-methoxy-5-sulfobenzophenone, and cyanoacrylate derivatives such as 2-ethylhexyl-2-cyano-3,3'-diphenylacrylate and ethyl-2-cyano-3,3'-diphenylacrylate. An example of commercial products of the organic ultraviolet-ray-absorbing agent is TINUVIN327 (trade name) made by Ciba-Geigy Co.

In the invention, the interlayer film may contain an organic heat-absorbing agent(s). Examples of this agent are NIR-AM1 made by Teikoku Chemical Industries, Ltd., and as near infrared rays absorbing agents SIR-114, SIR-128, SIR-130, SIR-132, SIR-169, SIR-103, PA-1001 and PA-1005 which are made by Mitsui Toatsu Chemicals, Inc. The interlayer film may further contain a pigment(s).

A laminated glass according to the present invention can be used as an architectural window glass or an automotive window glass such as a front windshield, a rear windshield with or without a shade band, a side windshield, or a sunroof.

In general, the sheet (surface) resistivity of a glass plate with glass antenna is preferably at least 20 k$\Omega$/□. In particular, when the glass plate is in contact with the antenna, the sheet resistivity is preferably at least 10 M$\Omega$/□. If it is less than 10 M$\Omega$/□, the difference between the sheet resistivity of a laminated glass and that of a glass plate itself may be at least 1 dB as an absolute value. The sheet resistivity of the laminated glass is preferably at least 15 M$\Omega$/□ for maintaining this difference within 0.8 dB (absolute value). The sheet resistivity of the laminated glass is preferably within a range from about 20 M$\Omega$/□ to about 10 G$\Omega$/□ and more preferably within a range from about 22 M$\Omega$/□ to about 10 G$\Omega$/□ for obtaining a satisfactory radio wave transmittance, satisfactory optical characteristics and satisfactory physical and chemical characteristics.

In the invention, it is possible to obtain a laminated glass which is superior in radio wave transmittance, heat insulation, ultraviolet rays insulation and optical characteristics. This laminated glass is particularly suitable as an automotive windshield. In more detail, this laminated glass as an automotive windshield has a radio transmittance which is equivalent to that of a glass plate itself, a solar radiation transmittance of up to 65% thereby improving a so-called automotive inhabitability, a visible light transmittance of at least 65% or at least 70% thereby allowing the driver and a passenger(s) to have a good view, and a very low visible light reflectance thereby allowing the driver and a passenger(s) to have a good view, avoid misreading of traffic control signal and the like, and minimize the eye fatigue. As an automotive glass plate, it is preferable that the laminated glass has a visible light transmittance of at least 68 or 70%, a visible light reflectance of up to 14%, a solar radiation transmittance of up to 60%, and an excitation purity of up to 15 or 10%. As an architectural glass plate, it is preferable that the laminated glass has a visible light transmittance of at least 30%, a visible light reflectance of up to 20%, a solar radiation transmittance of up to 65%, and an excitation purity of up to 20%.

The arrangement of the interlayer film is flexible according to need. In other words, for example, the interlayer film may be sized and arranged such that the interlayer film is not formed on a position corresponding to the peripheral portion of the laminated glass, nor on a position corresponding to the feeding point(s), nor on a position corresponding to a portion on which a molding is formed, nor on a position corresponding to the whole or a part of the electric conductor portion of an antenna.

According to the invention, the interlayer film has a heat insulation characteristic and a high sheet-resistivity equivalent to that of a semiconductor film or of an insulating film. Therefore, the laminated glass of the invention does not cause radio disturbance in receiving AM radio waves, FM radio waves and the like, nor radio interference such as ghost image of the TV picture. Even in case that a film which has a high resistivity and a heat insulation characteristic is formed on a glass antenna device, the radio receiving capacity of the laminated glass is not be lowered.

The first and second glass plates of the laminated glass may be made of an organic glass or a composite glass of inorganic and organic materials and may be colorless or colored float glass plates. This colored float glass plates may have a color of green, bronze, gray or blue. The first and second glass plates may be flat or curved and used for a multiple glass, a by-layer glass, or the like. In general, it is preferable that the first and second glass plates have a thickness, for example, from about 1.0 mm to about 12 mm. For architectural use, these plates have a thickness preferably from about 2.0 mm to about 10 mm. For automotive use, these plates have a thickness preferably from about 1.5 mm to about 3.0 mm and more preferably from about 2.0 mm to about 2.5 mm.

In the following, a method of producing a laminated glass will be described in detail in accordance with the present invention. This method comprises the steps of:

(a) interposing an interlayer film between first and second glass plates, the interlayer film having functional ultra-fine particles which are dispersed therein and have a particle diameter of up to 0.2 $\mu$m; and (b) bonding together the first and second glass plates and the interlayer film.

It is preferable that the step (b) is conducted in an autoclave by a common autoclave method, or under reduced pressure for a period of time from 20 to 30 minutes, while an ambient temperature was raised from 80 to 120° C. With this, the interlayer film will have uniformly uneven embossing thereon. However, in some cases, the step (b) may be conducted by one of various simpler methods.

In the following, a method of preparing the interlayer film will be described in detail in accordance with the present invention. This method comprises the steps of:

(c) dispersing up to 80.0 wt % of the functional ultra-fine particles in a plasticizer solution, based on the total weight of the plasticizer solution and the ultra-fine particles, so as to prepare a first mixture;

(d) adding up to 50 wt % of the first mixture to a PVB or to an EVA, based on the total weight of the PVB or EVA, so as to prepare a second mixture;

(e) optionally adding at least one additive to the second mixture so as to prepare a third mixture; and (f) kneading the third mixture to uniformly disperse therein the functional ultra-fine particles, thereby to prepare a raw material of the interlayer film.

During the step (c), the functional ultra-fine particles can be well uniformly dispersed in the plasticizer solution. Therefore, the first mixture becomes superior in transparency. During the step (c), if the amount of the functional ultra-fine particles exceeds 80.0 wt %, it becomes difficult to get uniformly dispersed ultra-fine particles. The amount of the ultra-fine particles is preferably up to about 20.0 wt %, more preferably up to about 10.0 wt %, and still more preferably within a range from 0.5 to 5.0 wt %. If the amount of the ultra-fine particles is too small, the advantageous effect of the addition may become insufficient.

During the step (d), if the amount of the first mixture exceeds 50 wt %, the ultra-fine particles may not be uniformly dispersed in the PVB or the EVA, and the interlayer film's basic characteristics may become unsatisfactory. During the step (d), the amount of the first mixture is preferably up to about 45 wt % and more preferably within a range from about 10 wt % to about 40 wt %. During the step (f), the third mixture is kneaded by a common mixer, Banbury mixer; Brabender plastograph, a kneader, or the like.

Examples of the plasticizer are phthalic acid esters such as dioctyl phthalate (DOP), diisodecyl phthalate (DIDP), ditridecyl phthalate and butylbenzyl phthalate (BBP), phosphoric acid esters such as tricresyl phosphate (TCP) and trioctyl phosphate (TOP), fatty acid esters such as tributyl citrate and methylacetyl ricinolate (MAR), polyether esters such as triethyleneglycol-di-2-ethylbutylate (3GH) and tetraethyleneglycoldihexanol, and mixtures of these compounds.

Examples of solvents for dissolving therein a PVB are ethyl alcohol, n-propyl alcohol, isopropyl alcohol, n-butyl alcohol and methylene chloride. Examples of solvents for dissolving therein an EVA are toluene, xylene and methylene chloride.

After the step (f), the raw material is shaped into the interlayer film using a common extruder, a calender or the like. The thickness of the interlayer film is preferably from about 0.2 to about 1.2 mm and more preferably from about 0.3 to about 0.9 mm.

There is provided an alternative method of preparing the interlayer film according to the present invention. This alternative method comprises the steps of:

(c) uniformly dispersing the functional ultra-fine particles having a particle diameter within a range from 0.001 to 0.2 μm, in a solvent which is capable of dissolving therein a PVB or an EVA, so that a first mixture is prepared;

(d) adding the PVB or the EVA, an optional plasticizer and at least one other optional additive to the first mixture, so that a second mixture in which the PVB or the EVA is dissolved is prepared;

(e) kneading the second mixture;

(f) shaping the kneaded second mixture into a wet film; and (g) drying the wet film at a temperature from 50 to 110° C. into the interlayer film.

There is provided a further alternative method of preparing the interlayer film in accordance with the present invention. This further alternative method comprises the steps of:

(c) heating a PVB or an EVA at a temperature which is higher than a glass transition temperature thereof, the glass transition temperature being within a range from 55 to 90° C., so that the PVB or the EVA is softened; and (d) adding functional ultra-fine particles having a particle diameter from 0.001 to 0.2 μm to the softened PVB or EVA, so that a first mixture is prepared; and (e) kneading the first mixture so as to uniformly disperse therein the functional ultra-fine particles, thereby preparing the raw material of the interlayer film.

The following examples are illustrative of the present invention, but these examples are not limitative.

EXAMPLE 1

In this example, an interlayer film was prepared as follows. At first, 10 g of a dioctyl phthalate solution containing 20 wt % of ATO (conductive antimony-containing tin oxide, ultra-fine particles which have a particle diameter up to 0.02 μm and are dispersed therein, and 130 g of pure dioctyl phthalate were added to 485 g of a polyvinyl butyral resin. Then, this mixture was kneaded at about 70° C. for about 15 min, with the addition of an ultraviolet ray absorbing agent and the like, by a mixer equipped with three rollers. The thus obtained raw material of the interlayer film was shaped at about 190° C. by an extruder into a film having a thickness of about 0.8 mm. With this, uniformly uneven embossing was formed on the surface of the interlayer film.

The thus prepared interlayer film was cut to have the same size as that of two clear glass substrates (FL2.3) having widths of about 300 mm and a thickness of about 2.3 mm. Then, the interlayer film was interposed between these glass substrates to prepare a laminate. Then, this laminate was put into a vacuum bag made of rubber. Then, the atmosphere of this bag was removed to reduce pressure thereof, and under this condition this bag was allowed to stand still for about 20–30 minutes at a temperature from about 80 to 110° C. Then, the temperature was lowered to room temperature. Then, the laminate was taken out of the bag and then put into an autoclave. Then, the laminate was heated at a temperature from about 110 to about 140° C. under a pressure from about 10 to about 14 kg/cm$^2$ for a period of time from about 20 to about 40 minutes for bonding together the glass substrates and the interlayer film.

The thus obtained laminated glass was subjected to several evaluation tests, as follows. In optical characteristics tests, the transmittance of the laminated glass for the light having a wavelength from 340 to 1,800 nm was measured with 340 type automated spectrophotometer (trade name) made by Hitachi Ltd. With this, the visible light transmittance Tv (380–780 nm), the solar radiation transmittance Ts (340–1,800 nm), excitation purity (Pe) and the color tone of the laminated glass were determined in accordance with Japanese Industrial Standard (JIS) Z 8722 and JIS R 3106 OR JIS Z 8701. In these tests, Tv was about 76.8%, Ts was about 58.6%, Pe was about 0.7%, and the color tone was a neutral pale gray. The laminated glass did not have glare caused by reflection.

The haze value (H) was determined in accordance with JIS K6714. Haze values of up to 3% and up to 1% were judged as being satisfactory as architectural and automotive laminated glasses, respectively. The result of this haze value test was about 0.3%.

In radio wave transmittance test, the value of reflection loss (dB) of the laminated glass within a radio wave frequency from 10 to 1,000 MHz was compared with that of a clear glass plate (FL3t) in accordance with the KEC method using an electric field shield effect meter. The laminated glass was judged as being satisfactory in this test, because the result of the laminated glass according to this example was equivalent to that of the clear glass plate, and because the absolute value of the difference therebetween was not greater than 2 dB.

In bond strength test, the laminated glass was allowed to stand still at a temperature from −18.6 to −17.4° C. for a period of time from 12 to 20 hr. Then, the laminated glass was hit by a hammer to break the glass plate thereof. The laminated glass was judged as being satisfactory, because the degree of exposure of the interlayer film was not significant.

In a heat resistance test, the laminated glass was put into boiling water at 100° C. for about 2 hr. The laminated glass was judged as being satisfactory, because the laminated glass, except its peripheral portion having a width of 10 mm, after this test did not have abnormalities such as the occurrence of bubbles, clouds, cracks and the like.

In a humidity resistance test, the laminated glass was allowed to stand still in an atmosphere of a temperature from 48 to 52° C. and a humidity from 91 to 99% for two weeks. The laminated glass was judged as being satisfactory, because the laminated glass after this test did not have abnormalities such as the occurrence of bubbles, clouds, crack and the like.

In an electrical characteristic test, the sheet resistivity of the laminated glass was measured with a surface resistivity meter (HIRESTA HT-210 (trade name) made by Mitsubishi Petrochemical Co., Ltd.). In this test, the laminated glass was judged as being satisfactory because it had a sheet resistivity of at least 10 MΩ/□.

In addition to the above-mentioned tests, a weatherability test and some other tests were conducted. The laminated glass was judged as being satisfactory in these tests, too. For example, the visible light transmittance was determined before and after the weatherability test for about 1,000 hr with a sunshine weathermeter. The laminated glass had substantially the same transmittance before and after this test. Therefore, it was judged as being satisfactory in this test.

EXAMPLE 2

In this example, an interlayer film was prepared as follows. At first, 10 g of a triethyleneglycol-di-2-ethylbutyrate (3GH) solution containing 20 wt % of ATO (conductive antimony-containing tin oxide) ultra-fine particles which have a particle diameter up to 0.02 μm and are dispersed therein, and 130 g of pure 3GH were added to 485 g of a polyvinyl butyral resin. Then, this mixture was kneaded at about 70° C. for about 15 min, with the addition of 5 g of a bond adjusting agent (TOSPEARL120 (trade name) made by Toshiba Silicone Co.), an ultraviolet ray absorbing agent and the like, by a mixer equipped with three rollers. The thus obtained raw material of the interlayer film was shaped at about 190° C. by an extruder into a film having a thickness of about 0.8 mm. With this, uniformly uneven embossing was formed on the surface of the interlayer film.

The thus prepared interlayer film was cut to have the same size as that of two clear glass substrates (FL2) having widths of about 300 mm and a thickness of about 2.0 mm. Then, the interlayer film was interposed between these glass substrates to prepare a laminate. Then, a laminated glass was prepared from this laminate in the same manner as in Example 1.

The same evaluation tests as those of Example 1 were conducted on the laminated glass. The laminated glass was satisfactory with respect to each evaluation test. For example, Tv was 76.5%, Ts was 58.5%, and H was 0.4%.

EXAMPLE 3

In this example, an interlayer film was prepared as follows. At first, 10 g of a butylbenzyl phthalate (BBP) solution containing 20 wt % of ITO (conductive tin-containing indium oxide) ultra-fine particles which have a particle diameter up to 0.1 μm and are dispersed therein, and 90 g of pure BBP were added to 323 g of a polyvinyl butyral resin. Then, from this mixture, an interlayer film having a thickness of about 0.8 mm was prepared in the same manner as in Example 1. With this, uniformly uneven embossing was formed on the surface of the interlayer film.

Using the thus prepared interlayer film and the same two glass substrates as those of Example 2, a laminated glass was prepared in the same manner as in Example 1.

The same evaluation tests as those of Example 1 were conducted on the laminated glass. The laminated glass was satisfactory with respect to each evaluation test. For example, Tv was 76.3%, Ts was 51.5%, and H was 0.4%. Furthermore, the pummel value was about 7–8. Therefore, the laminated glass was judged as being suitable as an architectural laminated glass.

EXAMPLE 4

In this example, Example 3 was repeated except in that 5 g of a bond adjusting agent (TOSPAL120 (trade name) made by Toshiba Silicone Co.) was additionally added in the preparation of the raw material of the interlayer film. Then, an interlayer film having a thickness of about 0.8 mm was prepared in the same manner as in Example 1. With this, uniformly uneven embossing was formed on the surface of the interlayer film.

Using the thus prepared interlayer film and the same two glass substrates as those of Example 2, a laminated glass was prepared in the same manner as in Example 1.

The same evaluation tests as those of Example 1 were conducted on the laminated glass. The laminated glass was satisfactory with respect to each evaluation test. For example, Tv was 76.2%, Ts was 51.6%, and H was 0.4%. Furthermore, the pummel value was about 3–4. Therefore, the laminated glass was judged as being suitable as an automotive laminated glass.

EXAMPLE 5

In this example, Example 3 was repeated except in that 10 g of an organic heat-absorbing agent was additionally added in the preparation of the raw material of the interlayer film. Then, an interlayer film having a thickness of about 0.8 mm was prepared in the same manner as in Example 1. With this, uniformly uneven embossing was formed on the surface of the interlayer film.

Using the thus prepared interlayer film and the same two glass substrates as those of Example 2, a laminated glass was prepared in the same manner as in Example 1.

The same evaluation tests as those of Example 1 were conducted on the laminated glass. The laminated glass was satisfactory with respect to each evaluation test. For example, Tv was 64.3%, Ts was 32.8%, and H was 0.4%.

EXAMPLE 6

In this example, an interlayer film was prepared as follows. At first, 7 g of a diisodecyl phthalate (DIDP) solution containing 20 wt % of ITO (conductive tin-containing indium oxide) ultra-fine particles which have a particle diameter up to 0.1 μm and are dispersed therein, and 95 g of pure DIDP were added to 323 g of a polyvinyl butyral resin. Then, from this mixture, an interlayer film having a thickness of about 0.8 mm was prepared in the same manner as in Example 1. With this, uniformly uneven embossing was formed on the surface of the interlayer film.

Using the thus prepared interlayer film, one glass substrate which is the same as one of those of Example 1, and another green glass substrate (NFL2), a laminated glass was prepared in he same manner as in Example 1.

The same evaluation tests as those of Example 1 were conducted on the laminated glass. The laminated glass was satisfactory with respect to each evaluation test. For example, Tv as 73.3%, Ts was 42.0%, and H was 0.2%.

EXAMPLE 7

In this example, Example 6 was repeated except in that 5 g of a bond adjusting agent (TOSPEARL120 (trade name) made by Toshiba Silicone Co.) was additionally added in the preparation of the raw material of the interlayer film. Then, an interlayer film having a thickness of about 0.8 mm was prepared in the same manner as in Example 1. With this, uniformly uneven embossing was formed on the surface of the interlayer film.

Using the thus prepared interlayer film and the same two glass substrates as those of Example 6, a laminated glass was prepared in the same manner as in Example 1.

The same evaluation tests as those of Example 1 were conducted on the laminated glass. The laminated glass was satisfactory with respect to each evaluation test. For example, Tv was 73.2%, Ts was 42.1%, and H was 0.2%.

EXAMPLE 8

In this example, Example 6 was repeated except in that the green glass substrate was replaced by a blue glass substrate (BFL2) in the preparation of the laminated glass.

The same evaluation tests as those of Example 1 were conducted on the laminated glass. The laminated glass was satisfactory with respect to each evaluation test. For example, Tv was 76.0%, Ts was 49.5%, and H was 0.2%.

EXAMPLE 9

In this example, Example 6 was repeated except in that the green glass substrate was replaced by a bronze glass substrate (MFL2) in the preparation of the laminated glass.

The same evaluation tests as those of Example 1 were conducted on the laminated glass. The laminated glass was satisfactory with respect to each evaluation test. For example, Tv was 75.1%, Ts was 52.1%, and H was 0.2%.

EXAMPLE 10

In this example, Example 6 was repeated except in that the green glass substrate was replaced by a gray glass substrate (GFL2) in the preparation of the laminated glass.

The same evaluation tests as those of Example 1 were conducted on the laminated glass. The laminated glass was satisfactory with respect to each evaluation test. For example, Tv was 76.0%, Ts was 54.5%, and H was 0.2%.

EXAMPLE 11

In this example, an interlayer film was prepared as follows. At first, 20 g of a DOP solution and 120 g of pure tricresyl phosphate (TCP) were added to 480 g of a polyvinyl butyral resin to prepare a mixture. This DOP solution contained 40 wt % of TM3410 (trade name) made by Dainichi Seika Kogyo Co., that is, ultra-fine particles of an inorganic pigment mixture of $Co_2O_3$ and $Al_2O_3$, which have a particle diameter from 0.01 to 0.02 μm and are dispersed in the solution. Then, an interlayer film having a thickness of about 0.8 mm was prepared from the above mixture in the same manner as in Example 1. Using the thus prepared interlayer film, a laminated glass was prepared in the same manner as in Example 1.

The same evaluation tests as those of Example 1 were conducted on the laminated glass. The laminated glass was satisfactory with respect to each evaluation test. For example, Tv was 73.8%, Ts was 50.2%, Pe was 7.8%, and H was 0.2%. The laminated glass had a clear blue color tone.

EXAMPLE 12

In this example, an interlayer film was prepared as follows. At first, 30 g of a DOP solution and 100 g of pure methylacetyl ricinolate (MAR) were added to 480 g of a polyvinyl butyral resin to prepare a mixture. This DOP solution contained 30 wt % of TM3320 (trade name) made by Dainichi Seika Kogyo Co., that is, ultra-fine particles of an inorganic pigment mixture of $TiO_2$, NiO, $Co_2O_3$ and ZnO which have a particle diameter from 0.01 to 0.02 μm and are dispersed in the solution. Then, an interlayer film having a thickness of about 0.8 mm was prepared from the above mixture in the same manner as in Example 1. Using the thus prepared interlayer film, a laminated glass was prepared in the same manner as in Example 1.

The same evaluation tests as those of Example 1 were conducted on the laminated glass. The laminated glass was satisfactory with respect to each evaluation test. For example, Tv was 77.8%, Ts was 60.2%, and H was 0.2%. Pe was 13.8%, and thus the laminated glass had a clear green color tone.

EXAMPLE 13

In this example, an interlayer film was prepared as follows. At first, 20 g of a DOP solution and 150 g of pure 3GH were added to 480 g of a polyvinyl butyral resin to prepare a mixture. This DOP solution contained 30 wt % of TM3210 (trade name) made by Dainichi Seika Kogyo Co., that is, ultra-fine particles of an inorganic pigment mixture of $Fe_2O_3$, ZnO and $Cr_2O_3$ which have a particle diameter from 0.01 to 0.02 μm and are dispersed in the solution. Then, an interlayer film having a thickness of about 0.8 mm was prepared from the above mixture in the same manner as in Example 1. Using the thus prepared interlayer film, a laminated glass was prepared in the same manner as in Example 1.

The same evaluation tests as those of Example 1 were conducted on the laminated glass. The laminated glass was satisfactory with respect to each evaluation test. For example, Tv was 67.8%, Ts was 51.8%, and H was 0.2%. Pe was a slightly high value, but the laminated glass had a clear green color tone.

EXAMPLE 14

In this example, an interlayer film was prepared as follows. At first, 10 g of a methylethyl ketone solution containing 20 wt % of the ATO ultra-fine particles dispersed in the solution, and 150 g of pure 3GH were added to 490 g of a polyvinyl butyral resin. Then, this mixture was kneaded, with the addition of the bond adjusting agent, the ultraviolet ray absorbing agent and the like, by a mixer equipped with three rollers, at about 80° C. under a pressure of about 20 mm Hg for about 1 hr. Then, from this kneaded mixture, an interlayer film having a thickness of about 0.8 mm was prepared in the same manner as in Example 1. Using the thus prepared interlayer film, a laminated glass was prepared in the same manner as in Example 1.

The same evaluation tests as those of Example 1 were conducted on the laminated glass. The laminated glass was satisfactory with respect to each evaluation test. For example, Tv was 76.4%, Ts was 51.6%, and H was 0.4%.

EXAMPLE 15

In this example, an interlayer film was prepared as follows. At first, 490 g of a polyvinyl butyral resin was heated at about 100° C. such that this resin became a syrupy condition. Under this condition, 2 g of the ATO ultra-fine particles were added to this resin. Then, this mixture was kneaded, with the addition of the ultraviolet ray absorbing agent and the like, by a mixer equipped with three rollers, at about 80° C. for about 1 hr. Then, from this kneaded mixture, an interlayer film having a thickness of about 0.8 mm was prepared in the same manner as in Example 1. Using the thus prepared interlayer film, a laminated glass was prepared in the same manner as in Example 1.

The same evaluation tests as those of Example 1 were conducted on the laminated glass. The laminated glass was satisfactory with respect to each evaluation test. For example, Tv was 77.5%, Ts was 55.7%, and H was 0.2%.

It is needless to say that pummel values of the laminated glasses of Examples 1, 2 and 5–15 can be adjusted for use as an architectural or automotive laminated glass.

What is claimed is:

1. A laminated glass comprising:

first and second transparent glass plates;

an interlayer film interposed between said first and second glass plates, said interlayer film comprising a polyvinyl butyral or an ethylene-vinylacetate copolymer; and functional ultra-fine particles which have a particle diameter of up to 0.2 μm and are dispersed in said interlayer film, said functional ultra-fine particles comprising at least one member selected from the group consisting of an antimony-doped tin oxide and a tin-doped indium oxide.

2. A laminated glass according to claim 1; wherein said interlayer film has a thickness from 0.2 to 1.2 mm.

3. A laminated glass according to claim 1, wherein said ultra-fine particles are in an amount from 0.01 to 10.0 wt %, based on the total weight of said interlayer film.

4. A laminated glass according to claim 1, wherein said functional ultra-fine particles have a particle diameter within a range from 0.001 to 0.15 μm.

5. A laminated glass according to claim 1, wherein said functional ultra-fine particles are mixed with an organic resin.

6. A laminated glass according to claim 1, wherein said interlayer film further comprises at least one member selected from the group consisting of organic ultraviolet-ray-absorbing agents, organic heat-absorbing agents and pigments.

7. A laminated glass according to claim 1, which can transmit radio waves and has a sheet resistivity within a range from 20 MΩ/□ to 10 GΩ/□.

8. A laminated glass according to claim 1, wherein said functional ultra-fine particles comprise a conductive antimony-containing tin oxide.

9. A laminated glass according to claim 1, wherein said functional ultra-fine particles comprise $SnO_2$ doped with Sb.

10. A laminated glass according to claim 1, wherein said functional ultra-fine particles comprise an indium tin oxide.

11. A laminated glass according to claim 1, wherein said functional ultra-fine particles comprise a conductive tin-containing indium oxide.

12. A laminated glass according to claim 1, where in said functional ultra-fine particles comprise $In_2O_3$ doped with Sn.

13. An architectural glass comprising the laminated glass according to claim 1, wherein said functional ultra-fine particles are in an amount from 0.01 to 9 wt % based on the total weight of said interlayer film.

14. An automotive window glass comprising the laminated glass according to claim 1, wherein said functional ultra-fine particles are in an amount from 0.01 to 2.0 wt %, based on the total weight of said interlayer film.

* * * * *